(12) United States Patent
Nie et al.

(10) Patent No.: US 11,540,828 B2
(45) Date of Patent: Jan. 3, 2023

(54) ADJUSTMENT MECHANISM FOR ADJUSTING FORMED STAPLE HEIGHT OF SUTURE STAPLE IN STAPLER AND STAPLER COMPRISING SAME

(71) Applicants: SHANGHAI YISI MEDICAL TECHNOLOGY CO., LTD., Shanghai (CN); YISI (SUZHOU) MEDICAL TECHNOLOGY CO., LTD., Suzhou (CN)

(72) Inventors: Honglin Nie, Shanghai (CN); Guang Yang, Shanghai (CN); Xiliang Zhang, Shanghai (CN); Xiufeng Shi, Shanghai (CN); Anhua Li, Shanghai (CN)

(73) Assignees: SHANGHAI YISI MEDICAL TECHNOLOGY CO., LTD., Shanghai (CN); YISI (SUZHOU) MEDICAL TECHNOLOGY CO., LTD., Jiangsu (CN)

( * ) Notice: Subject to any disclaimer, the term of this patent is extended or adjusted under 35 U.S.C. 154(b) by 9 days.

(21) Appl. No.: 16/320,319

(22) PCT Filed: Jun. 27, 2017

(86) PCT No.: PCT/CN2017/090327
§ 371 (c)(1),
(2) Date: Jan. 24, 2019

(87) PCT Pub. No.: WO2018/019072
PCT Pub. Date: Feb. 1, 2018

(65) Prior Publication Data
US 2019/0269404 A1 Sep. 5, 2019

(30) Foreign Application Priority Data
Jul. 28, 2016 (CN) .......................... 201610604904.4

(51) Int. Cl.
*A61B 17/072* (2006.01)

(52) U.S. Cl.
CPC ...... *A61B 17/07207* (2013.01); *A61B 17/072* (2013.01); *A61B 2017/07257* (2013.01);
(Continued)

(58) Field of Classification Search
CPC ............ A61B 17/07207; A61B 17/072; A61B 2017/07257; A61B 2017/07271;
(Continued)

(56) References Cited

U.S. PATENT DOCUMENTS 4,319,576 A * 3/1982 Rothfuss .............. A61B 17/115
227/175.3
4,527,724 A * 7/1985 Chow .................. A61B 17/072
227/8
(Continued)

FOREIGN PATENT DOCUMENTS

CN 101675895 A 3/2010
CN 102512222 A 6/2012
(Continued)

OTHER PUBLICATIONS

International Search Report and Written Opinion dated Sep. 15, 2017 in International Application PCT/CN2017/090327.
(Continued)

*Primary Examiner* — Robert F Long
(74) *Attorney, Agent, or Firm* — Venable LLP

(57) ABSTRACT

An adjustment mechanism for adjusting a formed staple height of a suture staple in a stapler comprises a first handle portion and a second handle portion. The first handle portion comprises a cartridge support located at a distal end, a cartridge assembly, a drive assembly, and the adjustment mechanism for adjusting a formed staple height of a suture staple, and the second handle portion comprises an anvil
(Continued)

located at a distal end. The cartridge assembly comprises suture staples, and the drive assembly can drive a suture staple to leave the cartridge assembly to reach the anvil to be pressed and formed. The adjustment structure adjusts a distance between the drive assembly and the anvil to adjust a formed staple height of a suture staple in a stapler. This application further relates to a stapler, comprising the adjustment mechanism for adjusting a formed staple height of a suture staple in a stapler.

15 Claims, 6 Drawing Sheets

(52) U.S. Cl.
CPC ............... *A61B 2017/07271* (2013.01); *A61B 2017/07278* (2013.01)

(58) Field of Classification Search
CPC .. A61B 2017/07278; A61B 2017/0725; A61B 2017/07285
USPC ............................................ 227/175.1–182.1
See application file for complete search history.

(56) References Cited

U.S. PATENT DOCUMENTS

| | | | |
|---|---|---|---|
| 4,608,981 A | 9/1986 | Rothfuss et al. | |
| 4,930,674 A * | 6/1990 | Barak ................... | A61B 17/072 227/179.1 |
| 5,074,454 A * | 12/1991 | Peters ............... | A61B 17/07207 227/178.1 |
| 5,271,543 A * | 12/1993 | Grant ................... | A61B 17/115 227/179.1 |
| 7,464,847 B2 * | 12/2008 | Viola ............... | A61B 17/07207 227/175.2 |
| 7,770,771 B2 * | 8/2010 | Tsai ...................... | B25C 5/1658 227/139 |
| 8,540,133 B2 | 9/2013 | Bedi | |
| 8,714,430 B2 * | 5/2014 | Natarajan ............ | A61B 17/068 227/176.1 |
| 8,925,782 B2 * | 1/2015 | Shelton, IV ......... | A61B 17/064 227/176.1 |
| 10,363,032 B2 * | 7/2019 | Scheib ................. | A61B 17/068 |
| 2010/0072251 A1 * | 3/2010 | Baxter, III ........... | A61B 17/105 227/175.2 |
| 2010/0072256 A1 | 3/2010 | Baxter et al. | |
| 2011/0139852 A1 * | 6/2011 | Zingman .............. | A61B 17/115 227/176.1 |
| 2011/0226837 A1 * | 9/2011 | Baxter, III ........... | A61B 17/115 227/175.1 |
| 2012/0223123 A1 | 9/2012 | Baxter et al. | |
| 2012/0312860 A1 * | 12/2012 | Ming ..................... | A61B 90/92 227/176.1 |
| 2014/0014705 A1 | 1/2014 | Baxter | |
| 2014/0042205 A1 | 2/2014 | Baxter et al. | |
| 2015/0066056 A1 * | 3/2015 | Cabrera Aquino ........................ A61B 17/12013 606/140 |
| 2016/0199089 A1 * | 7/2016 | Hess ............... | A61B 17/320016 227/180.1 |
| 2016/0374678 A1 * | 12/2016 | Becerra ............ | A61B 17/07207 227/177.1 |
| 2017/0086847 A1 * | 3/2017 | DiNardo .............. | A61B 17/105 |
| 2017/0105736 A1 * | 4/2017 | Chen .................. | A61B 17/1155 |
| 2017/0367701 A1 * | 12/2017 | Park ................. | A61B 17/07207 |
| 2019/0105053 A1 * | 4/2019 | Swayze .............. | A61B 17/1155 |
| 2020/0214698 A1 * | 7/2020 | Nie ...................... | A61B 17/068 |
| 2020/0315620 A1 * | 10/2020 | Nie ...................... | A61B 17/072 |
| 2022/0233192 A1 * | 7/2022 | Williams ............. | A61B 17/072 |

FOREIGN PATENT DOCUMENTS

| | | |
|---|---|---|
| CN | 102933159 A | 2/2013 |
| CN | 103169513 A | 6/2013 |
| CN | 103517679 A | 1/2014 |
| CN | 106108965 A | 11/2016 |

OTHER PUBLICATIONS

Office Action dated Apr. 9, 2021 in India Application 2624/2019/CHE.

* cited by examiner

ADJUSTMENT MECHANISM FOR ADJUSTING FORMED STAPLE HEIGHT OF SUTURE STAPLE IN STAPLER AND STAPLER COMPRISING SAME

CROSS REFERENCE TO RELATED APPLICATION

This application is a national stage application, filed under 35 U.S.C. § 371, of International Application No. PCT/CN2017/090327, filed on Jun. 27, 2017, entitled "CLOSED STAPLE HEIGHT ADJUSTING MECHANISM FOR STAPLER AND STAPLER COMPRISING SAID ADJUSTING MECHANISM," which claims priority to Chinese Patent Application No. 201610604904.4 filed on Jul. 28, 2016, which are incorporated herein by reference in their entirety.

TECHNICAL FIELD

This application relates to surgical instruments, and specifically, to an open-type adjustment mechanism for adjusting a formed staple height of a suture staple in a stapler and a stapler comprising the adjustment mechanism.

BACKGROUND ART

Currently, surgical staplers are increasingly widely applied to clinical surgeries and comprise linear staplers and circular staplers. The working principle of a surgical stapler is generally as follows: Two handle assemblies (one handle usually comprises an anvil assembly, and the other handle comprises a cartridge assembly) fitting each other are closed to hold tissue, and a suture staple in the cartridge assembly is then pushed out and formed to suture together the tissue. In some staplers, a cutting knife is further mounted. A plurality of rows of suture staples is stapled in body tissue and at the same time cut tissue between these rows of suture staples, so as to cut the sutured tissue.

A surgical stapler having the foregoing function comprises a first handle portion and a second handle portion. The first handle portion comprises a detachable cartridge assembly, a fixing rod, and a drive assembly. The cartridge assembly generally comprises a cartridge, several suture staples, several staple pushers. An upper surface of the cartridge is a tissue contact surface. A plurality of rows of holes is provided in the tissue contact surface. The suture staples are installed in the holes in advance. The second handle portion comprises an anvil. The anvil comprises a staple forming surface. A plurality of rows of staple forming slots is provided in the staple forming surface. The first handle portion and the second handle portion can be connected together, and are fixed through the fixing rod located at the first handle portion, so as to close tissue that needs to be sutured. The drive assembly in the first handle portion comprises a wedge-shaped push piece. When the drive assembly moves from a proximal end to a distal end of the stapler, the wedge-shaped push piece pushes the staple pushers, so as to push a suture staple in the cartridge out from a cartridge hole to penetrate closed tissue to reach the staple forming slots in the staple forming surface of the anvil to be pressed into a "B" shape. Generally, the drive assembly further comprises a cutting knife used to cut tissue between a plurality of rows of staple threads after the tissue is sutured with suture staples.

In many technical solutions, a formed staple height of a plurality of rows of suture staples in the stapler is fixed and is not adjustable. However, different parts of a human body portion have tissue with different thicknesses, and thicknesses also vary between people. Therefore, in some cases, if a formed staple height of a suture staple is excessively high, suture-hole bleeding may occur and a patient's life may be in jeopardy, and if a formed staple height of a suture staple is excessively low, tissue around cutting edges may die due to lack of blood supply, and as a result, the suture staples fall off and anastomotic leakage occurs.

Therefore, there is a pressing need for an improved surgical stapler with an adjustable formed staple height of a suture staple.

SUMMARY

In view of the foregoing deficiencies in the prior art, this application provides a novel adjustment mechanism for adjusting a formed staple height of a suture staple in a stapler, so that a stapler comprising the adjustment mechanism for adjusting a formed staple height of a suture staple can adjust a formed staple height of a suture staple of the stapler based on tissue having different characteristics, so that forming yields of suture staples are improved, an occurrence rate of phenomena such as suture-hole bleeding and anastomotic leakage is reduced.

To resolve the foregoing technical problem, the present disclosure describes embodiments that adopt the following technical solution:

A surgical stapler comprises a first handle portion and a second handle portion; the first handle portion comprises a cartridge support located at a distal end, a cartridge assembly, and a drive assembly, the cartridge assembly comprises suture staples, and the drive assembly can drive a suture staple to leave the cartridge assembly to reach an anvil to be pressed and formed; the second handle portion comprises the anvil located at a distal end; and the stapler further comprises an adjustment mechanism; and the adjustment structure adjusts a distance between the drive assembly and the anvil to adjust a formed staple height of a suture staple in the stapler.

In an implementation manner, the cartridge assembly can be detached from the cartridge support, and the cartridge assembly further comprises a cartridge and staple pushers disposed corresponding to the suture staples.

Further, the first handle portion further comprises a fixing rod located in the middle, and the first handle portion and the second handle portion can be fixed through the fixing rod after the distal ends of the first handle portion and the second handle portion are closed.

Further, a staple slot piece is disposed on the anvil, and the staple slot piece comprises a staple forming surface.

Further, the drive assembly comprises a push button and a push piece that is connected to the push button and has a wedge-shaped distal end; and the push button is pushed to push the push piece, the push piece having the wedge-shaped distal end drives the staple pushers one by one to move in a direction towards the anvil, and the staple pushers push a suture staple out from a cartridge hole to penetrate tissue closed by the first handle portion and the second handle portion to reach staple forming slots in the staple forming surface of the anvil to be pressed into a "B" shape.

The adjustment mechanism is placed at a bottom of the cartridge and comprises a cartridge support washer and an adjustment washer, an upper surface of the cartridge support washer fits a bottom surface of the push piece, the adjustment washer is placed below the cartridge support washer, and a bottom surface of the adjustment washer fits an upper surface of a bottom of the cartridge support; the adjustment washer is kept unchanged in a vertical direction and can move left and right in a horizontal direction, and the cartridge support washer is kept unchanged in the horizontal direction and can move up and down in the vertical direction; and a lower surface of the cartridge support washer comprises one or more first height adjustment regions, and each first height adjustment region at least comprises two step surfaces having unequal heights. The adjustment washer is moved in the horizontal direction, to enable an upper surface of the adjustment washer to be in contact with one of the step surfaces of the cartridge support washer, so as to adjust a height of the cartridge support washer, and further adjust a height of the push piece located above the cartridge support washer, so that a distance between the push piece and the anvil is changed. A formed staple height of a suture staple is determined by the distance between the push piece and the anvil. When the push piece is closer to the anvil, a formed staple height of the suture staple is smaller, and vice versa.

Further, second height adjustment regions are disposed on a region, corresponding to the first height adjustment regions on the cartridge support washer, on the upper surface of the adjustment washer. In an implementation manner, each second height adjustment region at least comprises one step surface.

In an implementation manner, the lower surface of the cartridge support washer comprises two first height adjustment regions, the upper surface of the adjustment washer comprises two second height adjustment regions, and a distance between the two second height adjustment regions is the same as a distance between the two first height adjustment regions.

In an implementation manner, each first height adjustment region comprises three step surfaces having unequal heights: a first step surface, a second step surface, and a third step surface, wherein the first step surface is the highest, that is, the cartridge support washer has a smallest width at the first step surface, the third step surface is the lowest, that is, the cartridge support washer has a largest width at the third step surface, and a height of the second step surface and a width of the cartridge support washer at the second step surface are both medium; and the adjustment washer is moved left and right in the horizontal direction, to enable the second height adjustment region to fit the first height adjustment region, so that the step surface of the adjustment washer fits one of the three step surfaces of the cartridge support washer, so as to adjust the height of the cartridge support washer in the vertical direction, thereby adjusting a distance between the push piece and the anvil and accordingly adjusting a formed staple height of a suture staple.

Further, when the step surface of the adjustment washer fits the first step surface of the cartridge support washer, the height of the cartridge support washer in the vertical direction is the lowest, the height of the push piece located above the cartridge support washer is also the lowest, and the distance between the push piece and the anvil is the largest; and the push piece pushes the staple pushers under the effect of the drive assembly to enable a suture staple in the cartridge hole to be pushed out from the cartridge, so that in this case a distance between a horizontal beam of the suture staple and the staple forming surface of the staple slot piece of the second handle portion is the largest and a height H1 obtained after the suture staple is formed is the highest. This case is suitable for stapling relatively thick tissue.

Further, when the step surface of the adjustment washer fits the second step surface of the cartridge support washer, the height of the cartridge support washer in the vertical direction is increased, the height of the push piece located above the cartridge support washer is also increased, and correspondingly, the distance between the push piece and the anvil becomes larger; and the push piece pushes the staple pushers under the effect of the drive assembly to enable a suture staple in the cartridge hole to be pushed out from the cartridge, so that in this case a distance between a horizontal beam of the suture staple and the staple forming surface of the staple slot piece of the second handle portion becomes shorter and as a result a height H2 obtained after the suture staple is formed is reduced, that is, H2<H1. This case is suitable for stapling tissue with a medium thickness.

Further, when the step surface of the adjustment washer fits and the third step surface of the cartridge support washer, the height of the cartridge support washer in the vertical direction is the highest, the height of the push piece located above the cartridge support washer is also the highest, and the distance between the push piece and the anvil is the smallest; and the push piece pushes the staple pushers under the effect of the drive assembly to enable a suture staple in the cartridge hole to be pushed out from the cartridge, so that in this case a distance between a horizontal beam of the suture staple and the staple forming surface of the staple slot piece of the second handle portion is the smallest and a height H3 obtained after the suture staple is formed is further reduced, that is, H3<H2<H1. This case is suitable for stapling relatively thin tissue.

In another implementation manner, the stapler comprises a plurality of rows of suture staples, and correspondingly comprises a plurality of rows of staple pushers disposed corresponding to the plurality of rows of suture staples. In this case, the drive assembly comprises one push piece. When being pushed, the push piece can push the plurality of rows of staple pushers at the same time, so as to push a plurality of rows of suture staples.

In still another implementation manner, the stapler comprises a plurality of rows of suture staples, and correspondingly comprises a plurality of rows of staple pushers disposed corresponding to the plurality of rows of suture staples. In this case, the drive assembly comprises a plurality of push pieces, wherein each push piece corresponds to one row of staple pushers. When being pushed, the push piece pushes the corresponding row of staple pushers, so as to push the row of suture staples corresponding to the push piece.

Further, the drive assembly further comprises a cutting knife, used to cut tissue between a plurality of rows of staple threads. For example, the drive assembly comprises two push pieces. The cutting knife is disposed between the two push pieces.

Further, the cutting knife is disposed at a proximal end of the two push pieces, so that when the push button is pushed towards a distal end, tissue is sutured with suture staples and is then cut.

Another aspect of this application further relates to a stapler, comprising the foregoing adjustment mechanism for adjusting a formed staple height of a suture staple.

In this application, by using a unique structural design, a formed staple height of a suture staple of a stapler can be adjusted, so that based on tissue having different characteristics, forming yields of suture staples can be improved, and an occurrence rate of phenomena such as suture-hole bleeding and anastomotic leakage can be reduced, thereby achieving efficient stapling of human tissue.

DETAILED DESCRIPTION

Figure 1:
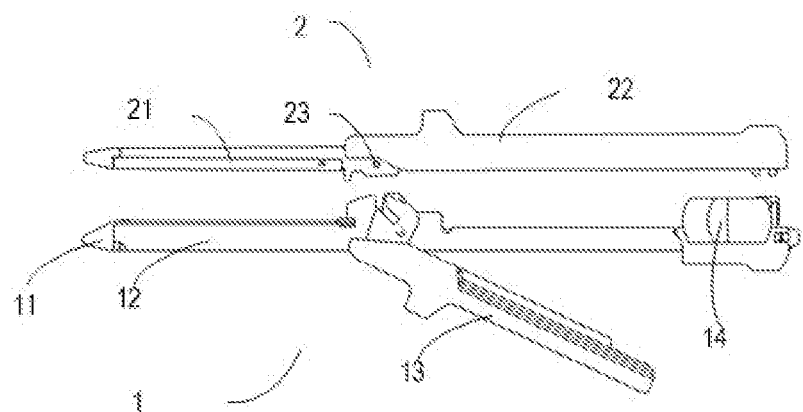
FIG. 1 is a side view of a surgical stapler according to an implementation manner of this application, wherein a first handle and a second handle are in a separated state.

Specific implementation manners of this application are described below in detail with reference to the accompanying drawings. To highlight related details of this application, well known parts and connection relationships in the field of exemplary implementation manners of this application are not described in detail or are omitted. In the accompanying drawings, the same reference numerals are used to represent the same parts, and the accompanying drawings are not drawn in proportion. An end far away from an operator is usually a distal end, and an end near the operator is usually a proximal end. For clear description, the description is provided according to a position when a stapler is placed horizontally. However, it is well known in the field that the stapler can be operated in any position during actual use.

Referring to FIG. 1, FIG. 1 is a side view of a surgical stapler according to an implementation manner of this application. For clarity, wherein a first handle and a second handle are in a separated state. The surgical stapler according to an implementation manner of this application comprises a first handle portion 1 and a second handle portion 2. The first handle portion 1 and the second handle portion 2 may be assemble together. As shown in FIG. 1, a rotating shaft 23 is disposed in the middle of the second handle portion 2, and a groove is provided in a corresponding position of the first handle portion 1. The rotating shaft 23 is inserted in the groove and can rotate pivotally in the groove, so that distal ends of the first handle portion 1 and the second handle portion 2 can be opened or closed. The first handle portion 1 comprises a cartridge support 12 located at a distal end, a cartridge assembly, a fixing rod 13 located in the middle, a drive assembly, and an adjustment mechanism. The second handle portion 2 comprises an anvil 21. Specifically, referring to FIG. 5, a staple slot piece 211 is provided on the anvil 21. The staple slot piece 211 comprises a staple forming surface. The first handle portion 1 and the second handle portion 2 can be fixed through the fixing rod 13 on the first handle portion 1 after distal ends of the first handle portion 1 and the second handle portion 2 are closed.

Figure 2:
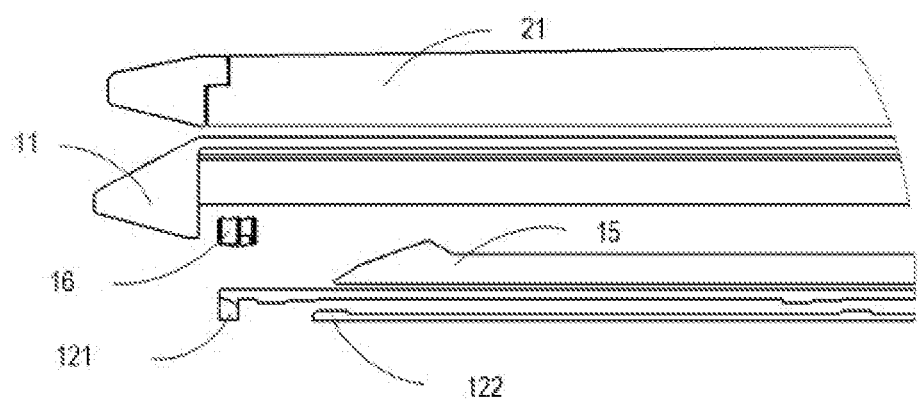
FIG. 2 is a schematic exploded view of distal parts of the surgical stapler shown in FIG. 1.
Figure 5:
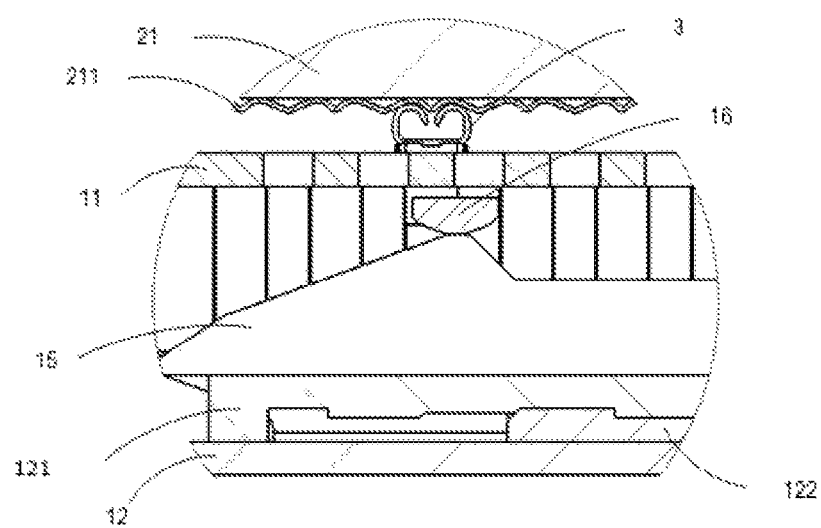
FIG. 5 is schematic partial enlarged view of a distal end of the surgical stapler shown in FIG. 1, wherein it is schematically shown that a push piece pushes a staple pusher to push a suture staple out from a cartridge hole and the suture staple reaches staple forming slots in a staple forming surface of an anvil to be pressed into a "B" shape.
Figure 7:
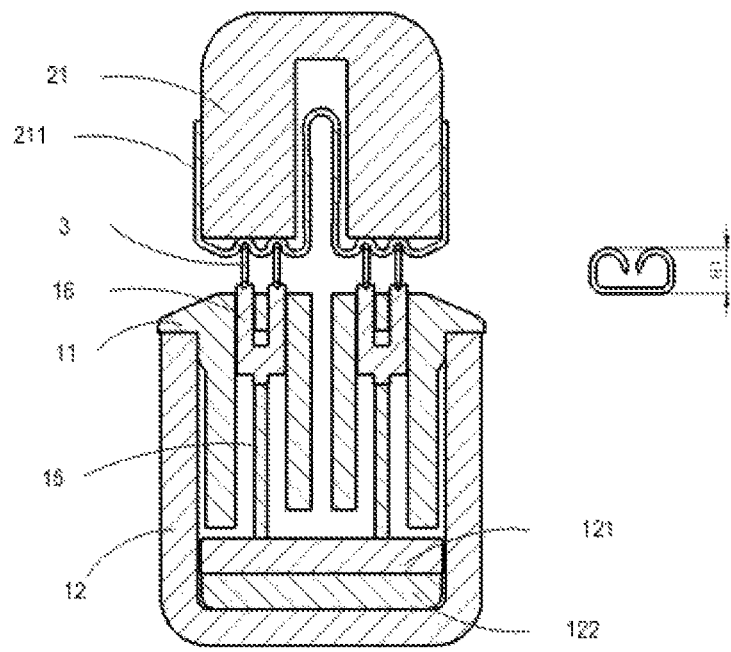
FIG. 7 is a front view of a distal end of the surgical stapler shown in FIG. 1, wherein the cartridge support washer and the adjustment washer are in a fit state shown in FIG. 6, that is, the step surface of the adjustment washer fits the first step surface of the cartridge support washer.

In an implementation manner, the cartridge assembly can be detached from the cartridge support 12. Referring to FIG. 2, FIG. 5, and FIG. 7, the cartridge assembly specifically comprises a cartridge 11, several staple pushers 16, and several suture staples 3 disposed corresponding to the staple pushers 16.

Referring to FIG. 1, FIG. 2, and FIG. 5, the drive assembly specifically comprises a push button 14 and a push piece 15 that is connected to the push button 14 and has a wedge-shaped distal end. The push button 14 is pushed horizontally to push the push piece 15. The push piece 15 having the wedge-shaped distal end drives the staple pushers 16 one by one to move in a direction towards the anvil 21. The staple pushers 16 pushes a suture staple 3 out from a cartridge hole to penetrate tissue closed by the first handle portion 1 and the second handle portion 2 to reach staple forming slots in the staple forming surface of the anvil 21 to be pressed into a "B" shape. Specifically, referring to FIG. 5, a formed staple height of a suture staple 3 is determined by the distance between the push piece 15 and the anvil 21. When the push piece 15 is closer to the anvil 21, a formed staple height of a suture staple 3 is smaller, and vice versa.

In another implementation manner, the drive assembly further comprises a cutting knife (not shown) used to cut tissue between a plurality of rows of staple threads. For example, referring to FIG. 7, the cutting knife may be disposed between two push pieces 15. The cutting knife is disposed between proximal ends of the two push pieces 15, so that when the push button 14 is pushed towards a distal end, the tissue is sutured with the suture staples 3 and is then cut.

Referring to FIG. 2, the adjustment mechanism is placed at a bottom of the cartridge 11 and comprises a cartridge support washer 121 and an adjustment washer 122. An upper surface of the cartridge support washer 121 fits a bottom surface of the push piece 15. The adjustment washer 122 is placed below the cartridge support washer 121. A bottom surface of the adjustment washer 122 fits an upper surface of a bottom of the cartridge support 12. A lower surface of the cartridge support washer 121 comprises one or more first height adjustment regions. Each first height adjustment region at least comprises two step surfaces having unequal heights. Second height adjustment regions are disposed on a region, corresponding to the first height adjustment regions on the cartridge support washer 121, on an upper surface of the adjustment washer 122. Each second height adjustment region at least comprises one step surface 1221.

Figure 3:
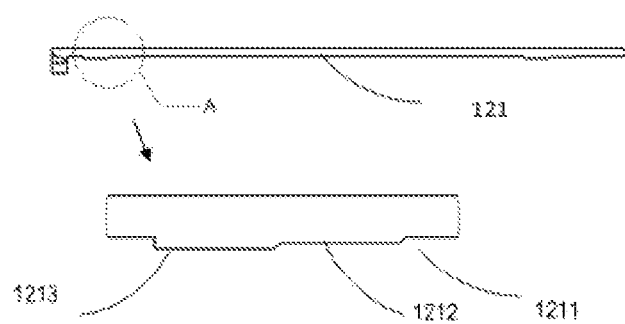
FIG. 3 is a side view of a cartridge support washer of the surgical stapler shown in FIG. 1, wherein a distal portion A of the cartridge support washer is shown in enlarged view.

In the implementation manner shown in FIG. 2 to FIG. 11, specifically, as shown in FIG. 3, the lower surface of the cartridge support washer 121 comprises two first height adjustment regions. Each first height adjustment region comprises three step surfaces having unequal heights: a first step surface 1211, a second step surface 1212, and a third step surface 1213. The first step surface 1211 is the highest, that is, the cartridge support washer 121 has a smallest width at the first step surface 1211, the third step surface 1213 is the lowest, that is, the cartridge support washer 121 has a largest width at the third step surface 1213, and a height of the second step surface 1212 and a width of the cartridge support washer 121 at the second step surface 1212 are both medium.

Figure 4:
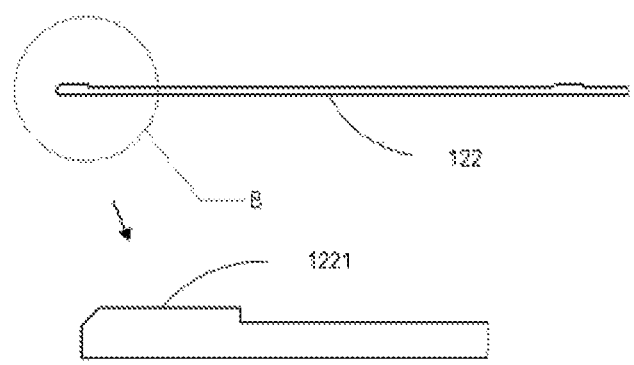
FIG. 4 is a structural side view of an adjustment washer of the surgical stapler shown in FIG. 1, wherein a distal portion B of the adjustment washer is shown in enlarged view.

In the implementation manner shown in FIG. 2 to FIG. 11, specifically, as shown in FIG. 4, the upper surface of the adjustment washer 122 comprises two second height adjustment regions. A distance between the two second height adjustment regions is the same as a distance between the two first height adjustment regions. Each second height adjustment region comprises one step surface 1221.

As shown in FIG. 5, the adjustment washer 122 is kept unchanged in a vertical direction and can move left and right in a horizontal direction. The cartridge support washer 121 is kept unchanged in the horizontal direction and can move up and down in the vertical direction. The adjustment washer 122 is moved left and right in the horizontal direction, to enable the second height adjustment region to fit the first height adjustment region, so that the step surface 1221 of the adjustment washer 122 fits one of the three step surfaces 1211 to 1213 of the cartridge support washer 121, so as to adjust a height of the cartridge support washer 121 in the vertical direction, thereby adjusting a distance between the push piece 15 and the anvil 21 and accordingly adjusting a formed staple height of a suture staple 3.

FIG. 6 to FIG. 11 show respectively front views from distal ends of the surgical stapler during working when the step surface 1221 of the adjustment washer 122 fits the first step surface 1211, the second step surface 1212 or the third step surface 1213 of the cartridge support washer 121. Formed suture staples 3 having different staple heights are shown on right sides in FIG. 7, FIG. 9, and FIG. 11.

Figure 6:
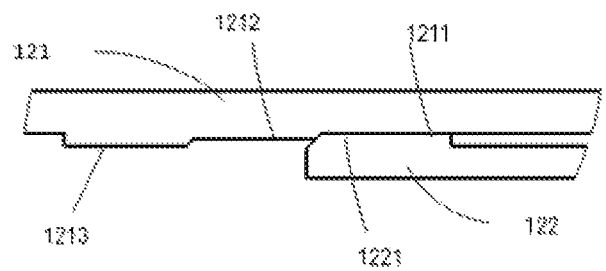
FIG. 6 is a side view of a cartridge support washer and an adjustment washer of the surgical stapler shown in FIG. 1, wherein a step surface of the adjustment washer fits a first step surface of the cartridge support washer.

Referring to FIG. 6 and FIG. 7, when the step surface 1221 of the adjustment washer 122 fits the first step surface 1211 of the cartridge support washer 121, the height of the cartridge support washer 121 in the vertical direction is the lowest, the height of the push piece 15 located above the cartridge support washer 121 is also the lowest, and the distance between the push piece 15 and the anvil 21 is the largest. The push piece 15 pushes the staple pushers 16 under the effect of the drive assembly to enable a suture staple 3 in the cartridge hole to be pushed out from the cartridge 11, so that in this case a distance between a horizontal beam of the suture staple 3 and the staple forming surface of the staple slot piece 211 of the second handle portion 2 is the largest and a height H1 obtained after the suture staple 3 is formed is the highest. This case is suitable for stapling relatively thick tissue.

Figure 8:
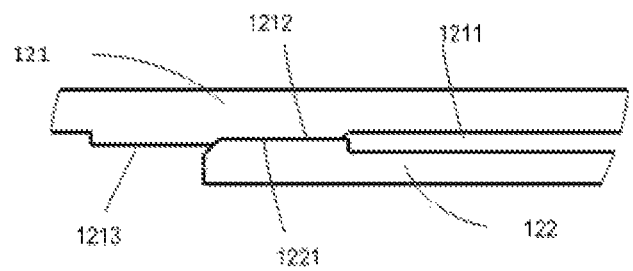
FIG. 8 is a side view of a cartridge support washer and an adjustment washer of the surgical stapler shown in FIG. 1, wherein a step surface of the adjustment washer fits a second step surface of the cartridge support washer.
Figure 9:
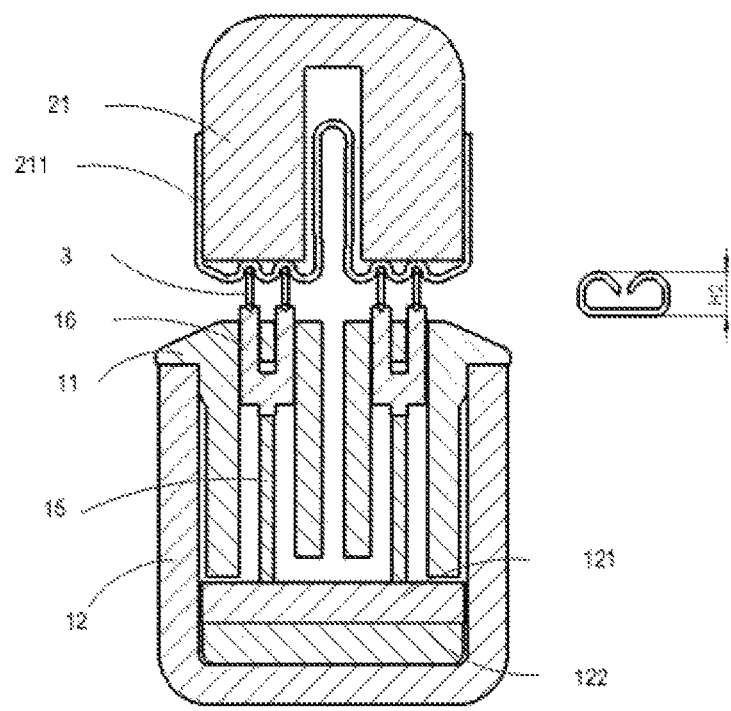
FIG. 9 is a front view of a distal end of the surgical stapler shown in FIG. 1, wherein the cartridge support washer and the adjustment washer are in a fit state shown in FIG. 8, that is, the step surface of the adjustment washer fits the second step surface of the cartridge support washer.

Referring to FIG. 8 and FIG. 9, when the step surface 1221 of the adjustment washer 122 fits the second step surface 1212 of the cartridge support washer 121, the height of the cartridge support washer 121 in the vertical direction is increased, the height of the push piece 15 located above the cartridge support washer 121 is also increased, and correspondingly, the distance between the push piece 15 and the anvil 21 becomes larger. The push piece 15 pushes the staple pushers 16 under the effect of the drive assembly to enable a suture staple 3 in the cartridge hole to be pushed out from the cartridge 11, so that in this case a distance between a horizontal beam of the suture staple 3 and the staple forming surface of the staple slot piece 211 of the second handle portion 2 becomes shorter and as a result a height obtained after the suture staple 3 is formed H2 is reduced, that is, H2<H1. This case is suitable for stapling tissue with a medium thickness.

Figure 10:
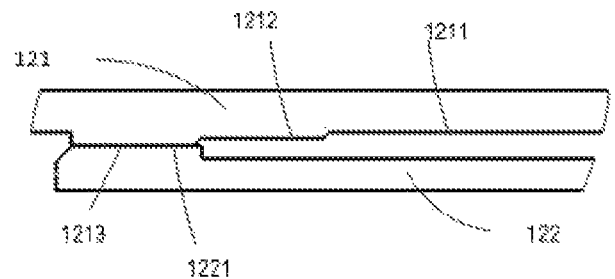
FIG. 10 is a side view of a cartridge support washer and an adjustment washer of the surgical stapler shown in FIG. 1, wherein a step surface of the adjustment washer fits a third step surface of the cartridge support washer.
Figure 11:
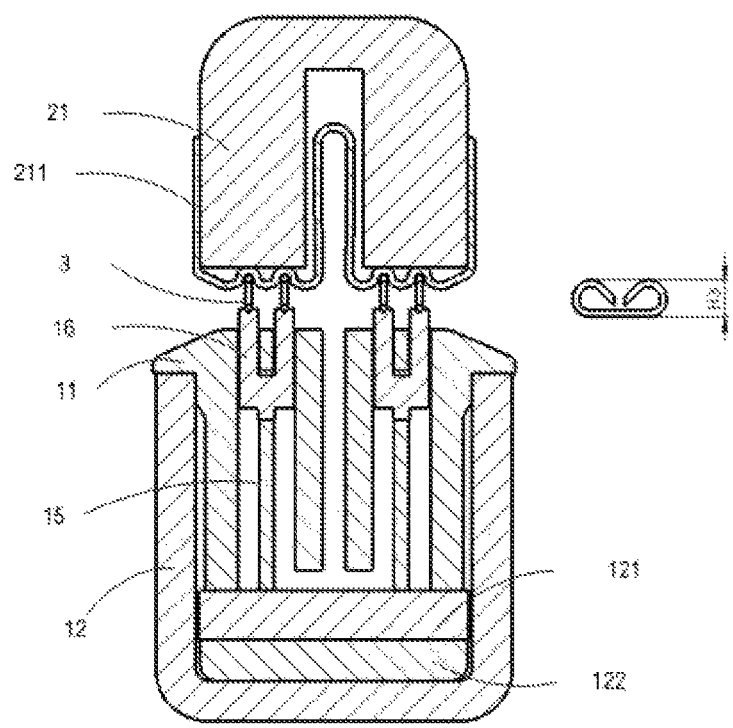
FIG. 11 is a front view of a distal end of the surgical stapler shown in FIG. 1, wherein the cartridge support washer and the adjustment washer are in a fit state shown in FIG. 10, that is, the step surface of the adjustment washer fits and the third step surface of the cartridge support washer.

Referring to FIGS. 10 and 11, when the step surface 1221 of the adjustment washer 122 fits the third step surface 1213 of the cartridge support washer 121, the height of the cartridge support washer 121 in the vertical direction is the highest, the height of the push piece 15 located above the cartridge support washer 121 is also the highest, and the distance between the push piece 15 and the anvil 21 is the smallest. The push piece 15 pushes the staple pushers 16 under the effect of the drive assembly to enable a suture staple 3 in the cartridge hole to be pushed out from the cartridge 11, so that in this case a distance between a horizontal beam of the suture staple 3 and the staple forming surface of the staple slot piece 211 of the second handle portion 2 is the smallest and a height H3 obtained after the suture staple 3 is formed is further reduced, that is, H3<H2<H1. This case is suitable for stapling relatively thin tissue.

It should be noted that the stapler in the example in this application is a linear stapler. However, this application is not only limited to being used in a linear stapler and can also be used in a circular stapler and another type of stapler. In addition, the implementation solutions in FIG. 1 to FIG. 11 are only relatively representative embodiments of this application. Persons skilled in the art may easily understand that the protection scope of this application is not merely limited to the ranges defined in the implementation manners, and combinations, deformations, and changes made to the implementation manners all fall within the protection scope of this application.

The invention claimed is:

1. A stapler capable of adjusting a formed staple height of a suture staple in the stapler, comprising:
    a first handle portion including a cartridge support located at a distal end, a cartridge assembly, a drive assembly, and an adjustment mechanism for adjusting the formed staple height of the suture staple; and
    a second handle portion including an anvil located at a distal end, wherein
    the cartridge assembly includes suture staples,
    the drive assembly is configured to drive the suture staples to leave the cartridge assembly to reach the anvil to be pressed and formed, and
    the adjustment mechanism is positioned at a bottom of the cartridge assembly and comprises a cartridge support washer and an adjustment washer placed below the cartridge support washer, an upper surface of the cartridge support washer fitting a bottom surface of one or more push pieces, a bottom surface of the adjustment washer fitting an upper surface of a bottom of the cartridge support, one or more first height adjustment regions fitting between the cartridge support washer and the adjustment washer capable to be adjusted to change the position of a portion of the drive assembly to adjust a distance between the portion of the drive assembly and the anvil, such that the formed staple height of the suture staples in the stapler is adjusted,
    wherein the adjustment mechanism is spaced apart from the anvil via the one or more push pieces,
    wherein a lower surface of the cartridge support washer comprises the one or more first height adjustment regions, wherein an upper surface of the adjustment washer is configured to be in contact with the one or more first height adjustment regions so as to adjust a height of the cartridge support washer, wherein the cartridge assembly further comprises a cartridge and staple pushers disposed corresponding to the suture staples; the drive assembly comprises a push button and the one or more push pieces that are connected to the push button and have a wedge-shaped distal end; and the push button is pushed to push the one or more push pieces, the one or more push pieces having the wedge-shaped distal end drive the staple pushers one by one to move in a direction towards the anvil, and the staple pushers push a suture staple out from a cartridge hole to penetrate tissue closed by the first handle portion and the second handle portion to reach the anvil to be pressed into a "B" shape, and wherein the adjustment washer is kept unchanged in a vertical direction and is configured to move left and right in a horizontal direction, and the cartridge support washer is kept unchanged in the horizontal direction and is configured to move up and down in the vertical direction, and wherein the adjustment washer is moved in the horizontal direction, to enable the upper surface of the adjustment washer to be in contact with the one or more first height adjustment regions, so as to adjust the height of the cartridge support washer, and further adjust a height of the one or more push pieces located above the cartridge support washer, so that a distance between the one or more push pieces and the anvil is changed.

2. The stapler according to claim 1, wherein each first height adjustment region of the one or more first height adjustment regions at least comprises two step surfaces having unequal heights, and the adjustment washer is moved in the horizontal direction, to enable the upper surface of the adjustment washer to be in contact with one of the step surfaces of the cartridge support washer, so as to adjust the height of the cartridge support washer.

3. The stapler according to claim 2, wherein one or more second height adjustment regions are disposed on a region, corresponding to the one or more first height adjustment regions on the cartridge support washer, on the upper surface of the adjustment washer.

4. The stapler according to claim 3, wherein the lower surface of the cartridge support washer comprises two first height adjustment regions, the upper surface of the adjustment washer comprises two second height adjustment regions, and a distance between the two second height adjustment regions is the same as a distance between the two first height adjustment regions.

5. The stapler according to claim 3, wherein each second height adjustment region of the one or more second height adjustment regions at least comprises one step surface.

6. The stapler according to claim 5, wherein each first height adjustment region of the one or more first height adjustment regions comprises three step surfaces having unequal heights: a first step surface, a second step surface, and a third step surface, wherein the first step surface is the highest, that is, the cartridge support washer has a smallest width at the first step surface, the third step surface is the lowest, that is, the cartridge support washer has a largest width at the third step surface, and a height of the second step surface and a width of the cartridge support washer at the second step surface are both medium; and the adjustment washer is moved left and right in the horizontal direction, to enable the second height adjustment region to fit the first height adjustment region, so that the step surface of the adjustment washer fits one of the three step surfaces of the cartridge support washer, so as to adjust the height of the cartridge support washer in the vertical direction, thereby adjusting a distance between the one or more push pieces and the anvil and accordingly adjusting a formed staple height of a suture staple.

7. The stapler according to claim 6, wherein a staple slot piece is disposed on the anvil, and the staple slot piece comprises a staple forming surface, wherein when the step surface of the adjustment washer fits the first step surface of the cartridge support washer, the height of the cartridge support washer in the vertical direction is the lowest, the height of the one or more push pieces located above the cartridge support washer is also the lowest, and the distance between the one or more push pieces and the anvil is the largest; and the one or more push pieces push the staple pushers under the effect of the drive assembly to enable a suture staple in the cartridge hole to be pushed out from the cartridge, so that in this case a distance between a horizontal beam of the suture staple and the staple forming surface of the staple slot piece of the second handle portion is the largest and a height $H1$ obtained after the suture staple is formed is the highest.

8. The stapler according to claim 7, wherein when the step surface of the adjustment washer fits the second step surface of the cartridge support washer, the height of the cartridge support washer in the vertical direction is increased, the height of the one or more push pieces located above the cartridge support washer is also increased, and correspondingly, the distance between the one or more push pieces and the anvil becomes larger;

and the one or more push pieces push the staple pushers under the effect of the drive assembly to enable a suture staple in the cartridge hole to be pushed out from the cartridge, so that in this case a distance between the horizontal beam of the suture staple and the staple forming surface of the staple slot piece of the second handle portion becomes shorter and as a result a height $H2$ obtained after the suture staple is formed is reduced, that is, $H2<H1$.

9. The stapler according to claim 8, wherein when the step surface of the adjustment washer fits and the third step surface of the cartridge support washer, the height of the cartridge support washer in the vertical direction is the highest, the height of the one or more push pieces located above the cartridge support washer is also the highest, and the distance between the one or more push pieces and the anvil is the smallest; and the one or more push pieces push the staple pushers under the effect of the drive assembly to enable a suture staple in the cartridge hole to be pushed out from the cartridge, so that in this case a distance between the horizontal beam of the suture staple and the staple forming surface of the staple slot piece of the second handle portion is the smallest and a height $H3$ obtained after the suture staple is formed is further reduced, that is, $H3<H2<H1$.

10. The stapler according to claim 1, wherein the cartridge assembly is configured to be detached from the cartridge support.

11. The stapler according to claim 1, wherein the first handle portion further comprises a fixing rod located in the middle, and the first handle portion and the second handle portion is configured to be fixed through the fixing rod after the distal ends of the first handle portion and the second handle portion are closed.

12. The stapler according claim 1, wherein a staple slot piece is disposed on the anvil, and the staple slot piece comprises a staple forming surface.

13. The stapler according to claim 1, wherein there are two rows of suture staples.

14. The stapler according to claim 13, wherein the one or more push pieces comprise two push pieces, and the drive assembly comprises a cutting knife disposed between the two push pieces.

15. The stapler according to claim 14, wherein the cutting knife is disposed at a proximal end of the two push pieces, so that when the push button is pushed towards a distal end, tissue is sutured with suture staples and is then cut.

* * * * *